United States Patent [19]

Ishimaru

[11] 4,046,759

[45] Sept. 6, 1977

[54] PENICILLIN ESTERS

[76] Inventor: Toshiyasu Ishimaru, D-14, 2-7, Momoyamadai, Suite, Japan

[21] Appl. No.: 607,362

[22] Filed: Aug. 25, 1975

[30] Foreign Application Priority Data

| Aug. 29, 1974 | Japan | 49-99580 |
| Oct. 18, 1974 | Japan | 49-120488 |
| Apr. 14, 1975 | Japan | 50-45448 |
| June 6, 1975 | Japan | 50-68879 |

[51] Int. Cl.$^2$ .................. C07D 499/58; C07D 499/44
[52] U.S. Cl. .................. 260/239.1; 424/271
[58] Field of Search .................. 260/239.1

[56] References Cited

U.S. PATENT DOCUMENTS

| 2,650,218 | 8/1953 | McDuffie et al. | 260/239.1 |
| 3,528,965 | 9/1970 | Cole et al. | 260/239.1 |
| 3,652,546 | 3/1972 | Cheney et al. | 260/239.1 |

OTHER PUBLICATIONS

Jansen et al., J. Chem. Soc. 2127-2132 (1965).

*Primary Examiner*—Gerald A. Schwartz
*Attorney, Agent, or Firm*—Hubbell, Cohen Stiefel & Gross

[57] ABSTRACT

There disclose new penicillin esters and S-oxides thereof which are of value as intermediates for the preparation of various cephalosporin antibiotics.

9 Claims, No Drawings

PENICILLIN ESTERS

This invention relates to new esters of penicillins and S-oxides thereof and a method for the same.

According to the invention, there are provided new penicillin esters and S-oxides thereof which can be represented by the following general formula (I):

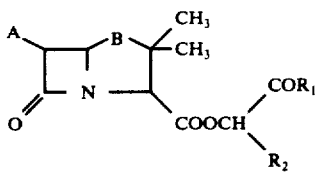
(I)

wherein A is an acylamino group; B is =S or =S—O; R₁ is a lower alkoxy, lower alkyl, aralkyl or aryl group; R₂ is a hydrogen atom or a lower alkyl, lower alkoxycarbonyl, lower alkylcarbonyl, aralkylcarbonyl or arylcarbonyl group or a group of the formula:

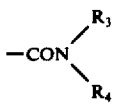

in which R₃ and R₄, which may be the same or different, are hydrogen atoms, aryl groups or lower alkyl groups which may form a heterocyclic ring together with an oxygen or nitrogen atom.

Ester parts of penicillin esters are necessarily removed at a suitable stage of penicillin or cephalosporin derivatives which are produced after desired reactions, with a few exceptions of esters themselves for the use of medicine. While, it is required to carry out de-esterification of penicillin or cephalosporin esters under a mild condition which does not accompany a decomposition of β-lactam ring and therefore the usable esters have been extremely limited. Also, in case of cephalosporin esters yielded by ring-enlargement of penicillin esters, their de-esterifications which are necessary for obtaining useful compounds as medicine are also limited to ones under the condition that a migration of the double bond in the cephem ring does not occur. Taking due considerations into such problems, the inventors found new esters of penicillins which are suitable for their subjecting to desired reactions as well as to subsequent de-esterification.

It is an object of the present invention to provide new penicillin esters which are industrially useful and also can suitably be utilized for desired reactions. Another object of the invention is to provide a method for preparing new penicillin esters which are of use as intermediates for important cephalosporins. Still other objects and features of the invention will become apparent in the following description.

The compounds (I) of the present invention may be prepared by reacting 6-acylaminopenicillanic acid or its 1-oxide having the general formula (II):

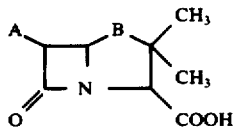
(II)

wherein A and B are the same meanings as defined above, or salt thereof with a halo compound of the general formula (III):

(III)

wherein X is a halogen atom, and B, R₁ and R₂ are the same meanings as defined above, and if desired, treating the resulting compound in which B is a sulfur atom, with an oxidizing agent to yield the corresponding S-oxide.

The acylamino groups in the formulae (I) and (II) way be arbitrary ones, e.g., phenylacetamido, phenoxyacetamido acetamido, propionamido, chloroacetamido, benzoylamino, phthalimido, 2,2,2-trichloroethoxycarbonylamino, benzyloxycarbonylamino and like groups. However, the preferred examples are phenylacetamido and phenoxyacetamido group.

As the salts of the compond (II) as the starting material may be mentioned the potassium, sodium, triethylamine, dicyclohexylamine, N-ethylpiperidine or N-methylpiperidine, N-methylmorphorine salts and the like. The potassium or sodium salt is usually employed.

Examples of the halo compounds (III) may be mentioned as follows:

i. α-halo lower aliphatic acid ester, such as methyl α-bromoacetate, ethyl α-bromoacetate, methyl α-bromopropionate, or methyl α-bromo-α-phenylacetate, or α-chloro compounds thereof, ii. α-halo keto-acid ester, such as methyl α-bromoacetoacetate ethyl α-bromoacetoacetate, i-butyl α-bromoacetoacetate or methyl α-bromo-α-phenylacetoacetate, or α-chloro compounds thereof, iii. halo-diketones, such as 3-bromo-2,4-pentandione, 1-bromo-1-phenyl-2,4-pentandione, 1-phenyl-2-bromo-1,3-pentandione, 1-phenyl-4-bromo-2,4-hexandione or 1-phenyl-2-bromo-1,3-butandione, or chloro compounds thereof, iv. α-haloketo-acid-amides such as α-bromoacetoacetamide, α-bromo-N-methylacetoacetamide, α-bromo-N,N-dimethylacetoacetamide, α-bromo-N,N-diethylacetoacetamide, α-bromo-N,N-dipropyl-acetoacetamide, α-bromo-N-phenylacetoacetamide, N-(α-bromoacetoacetyl)morpholide or N-(α-bromoacetoacetyl)piperidide, or chloro compounds thereof.

The preferred examples are 3-chloro (or bromo)-2,4-pentandione, methy α-chloro(or bromo)acetoacetate and ethyl α-chloro(or bromo)acetoacetate.

The reaction of 6-acylaminopenicillanic acid or its 1-oxide (II) or salt thereof with a halo compound (III) is usually conducted in an inert solvent. When the compound (II) is used as the free acid form, it is recommended to add an base such as triethylamine or N-methylmorpholine to the reaction system, by which the salt with such base is formed.

As examples of the inert solvents, may be mentioned methanol, ethanol, butanol, acetone, methyl isobutyl ketone, acetonitrile, dimethylformamide, dimethylacetamide, dimethylsufoxide, tetrahydrofuran, dioxane, methylene chloride, chloroform, carbon tetrachloride, ethylene chloride, trichloroethylene, trichloroethane, propylene chloride, ethylene glycol dimethylether, methyl acetate, ethyl acetate, propyl acetate, or butyl acetate. Preferred examples are dimethylformamide, dimethylacetamide, dimethylsulfoxide, acetone, methyl isobutyl ketone, methyl isopropyl ketone, methyl ethyl ketone, methylene chloride, trichloro ethylene, ethylene chloride or the like.

The reaction may be conducted at 0° ∼ 100° C, usually at 10° ∼ 60° C. The reaction time depends upon the reaction temperature, the kinds of the solvent snd the halo compound (III) or the like. The reaction with the halo compound (III) being a chloro compound will be accelerated by addition of a catalystic amount of sodium iodide or potassium iodide. The reaction may be monitored by a thin-layer chromatography (e.g., using a developing solvent of benzene: ethyl acetate = 2:1 and a coloring agent of iodoazide).

The resulting ester compounds wherein B is sulfur atom, when desired, may be converted into the corresponding S-oxide compounds by treatment with appropriate oxidizing agents. As the oxidizing agents may mentioned peracetic acid, perbenzoic acid, m-chloroperbenzoic acid, hydrogen peroxide or the like. The oxidation may proceed advantageously by addition of a catalyst such as vanadium oxide, molybdenum oxide or tungsten oxide. The solvents used herein are preferably dimethylformamide, dimethylsulfoxide, acetone, methanol, methyl isobutyl ketone, methyl isopropyl ketone, acetonitrile or the like.

Then resulted compounds (I) may be isolated in accordance with conventional methods. Generally, the S-oxide compounds, i.e., B being =S—O is either crystalline or oily. Furthermore, said S-oxide compounds may be converted into the corresponding cephem carboxylic acid esters in the treatment with appropriate catalysts, and the ester groups of the resulting cephem esters can be very easily hydrolyzed by the treatment with e.g., a base, or nitrous acid or its salts or ester, or nitorsyl halide.

The following examples are given for the purpose of illustrating the present invention.

EXAMPLE 1

To a suspension of 37.2 g (0.1 mol) of potassium 6-phenylacetamidopenicillanate and 1.0 g (0.01 mol) of potassium hydrogen carbonate in 50 ml of dimethylformamide, 18.8 g (0.105 mol) of 3-bromo-2,4-pentandione were gradually added while stirring under ice-cooling. Then, the mixture was gradually raised to ambient temperature. After monitoring the reaction mixture by TLC (benzene:ethyl acetate = 2:1, spraying on a solution of iodoazide and heating), 100 ml of methylene chloride were added to the mixture, which then was poured into 200 ml of ice-water and adjusted to pH 7.0 ∼ 7.5.

The aqueous layer was treated several times with methylene chloride. The combined organic layers were washed with water, dried and evaporated. The syrupy residue was difficult to crystallize. It was dissolved in methylene chloride and oxidized with 40% peracetic acid under ice-cooling, while monitoring by TLC. After completing the oxidation, 50 ml of ice-water were added to the mixture and adjusted to pH 7.5 with ammonia under stirring. The aqueous layer was treated with methylene chloride. The combined organic layers were washed with water, dried and evaporated in vacuo. The residue was treated with isopropanol and n-hexane to yield 39 g (yield: 87%) of 2′ 4′-dioxopentan-3′-yl ester of 6-phenylacetamidopenicillanic acid 1-oxide. The product was purified by silicagel column chromatography (benzene/ethyl acetate). mp 55° ∼ 60° C.

IR (KBr): 1800 ∼ 1730 cm$^{-1}$

Anal.; $C_{21}H_{24}N_2O_7S$ Calc.; C 56.24, H 5.39, N 6.25
Found; C 56.34, H 5.31, N 6.32,

EXAMPLE 2

To a suspension of 37.2 g of potassium 6-phenylacetamidopenicillanate in 40 ml of dimethylsulfoxide, 14.1 g of 3-chloro-2,4-pentandione were gradually dropwise added while stirring under ice-cooling. The mixture was treated as described in Example 1, yielding 2′,4′-dioxopentan-3′-yl 6-phenylacetamidopenicillanate-1-oxide in a yield of 95%.

EXAMPLE 3

2′,4′-Dioxopentan-3′-yl 6-phenoxyacetamidopenicillanate-1-oxide was prepared according to the procedure described in Example 1, using potassium 6-phenoxyacetamidopenicillanate instead of potassium 6-phenylacetamidopenicillanate in Example 1.

Yield: 87%, mp 145 ∼ 148° C, IR: 1790 cm$^{-1}$

EXAMPLE 4

To a suspension of 38 g of potassium 6-phenylacetamidopenicillanate and 1 g of potassium hydrogen carbonate in 40 ml of acetone and 40 ml of dimethylformamide, methyl α-chloroacetoacetate was dropwise added over a period of 30 minutes, while stirring at ambient temperature. (The reaction mixture became green gradually.)

The progress of the reaction was monitored by TLC (benzene: ethyl acetate = 2:1, spraying on a solution of iodoazide and heating). When needed, the mixture was warmed to 40° ∼ 50° C in a water-bath. After 4 ∼ 6 hours, the acetone was removed 100 ml of ethyl acetate and 200 ml of ice-water were added to the remaining mixture and adjusted to pH 7.3 under stirring. The organic layer was separated and the aqueous layer was extracted several times with ethyl acetate. The combined organic layers were washed with water, dried over magnesium sulfate and evaporated. 44 g (98%) of 1′-methoxycarbonyl-2′-oxopropan-1′-yl 6-phenylacetamidopenicillanate was thus obtained as an oil.

EXAMPLE 5

Into a suspension of 38 g of potassium 6-phenylacetamidopenicillanate and 1 g of potassium hydrogen carbonate in 60 ml of acetone and 50 ml of dimethylformamide was dropwise added methyl α-chloroacetacetate over a period of 30 minutes. The mixture was stirred at 45° ∼ 55° C in a water-bath. After confirming the completion (about 5 hours) of the reaction by TLC, the acetone was removed in vacuo. The remaining mixture was ice-cooled and subjected to oxidation with a calculated amount of 40% peracetic acid, and further peracetic acid when needed was supplemented. After the reaction was completed (TLC), 200 ml of ethyl acetate and 200 ml of ice-water were added to the mixture, which then was adjusted to pH 7.3 with ammonium carbonate. The aqueous layer was treated several times with ethyl acetate. The combined organic layers were washed with water, dried and evaporated in vacuo. The syrupy residue was treated with isopropyl ether. The resulted solid was recrystallized from ethanol and isopropyl ether to obtain 44 g (yield: 94%) of 1'-methoxycarbonyl-2'-oxopropanol-1-yl 6-phenylacetamidopenicillanate 1-oxide having mp. 134° ~ 135° C.
IR: 1800 cm$^{-1}$
Anal.; $C_{21}H_{24}N_2O_8S$ Calc.; C 54.30, H 5.21, N 6.03. Found; C 54.04, H 5.20, N 5.89.

EXAMPLE 6

1'-Ethoxycarbonyl-2'-oxopropan-1'-yl 6-phenylacetamidopenicillanate 1-oxide was prepared according to the procedure described in Example 4, using ethyl α-chloroacetoacetate instead of methyl α-chloroacetoacetate in Example 4.
Yield: 43 g (90%).

EXAMPLE 7

1'-Methoxycarbonyl-2'-oxopropan-1'-yl ester of 6-phenoxyacetamidophenicillanic acid 1-oxide was prepared according to the procedure described in Example 5, using potassium 6-phenoxyacetamidopenicillanate (39 g) instead of potassium 6-phenylacetamidopenicillante in Example 5.
Recrystallization from isopropyl alcohol and isopropyl ether gave the crystals of mp 65° ~ 67° C and IR: 1800 cm$^{-1}$
Yield: 93%

EXAMPLE 8

1'-Methoxycarbonyl-2'-oxopropan-1'-yl ester of 6-phenylacetamidopenicillanic acid 1-oxide was prepared according to the procedure described in Example 4, using methyl α-bromoacetoacetate instead of methyl α-chloroacetoacetate in Example 4. The reaction completed for 5 ~ 6 hours at ambient temperature, as its velocity with the bromo compound was faster than that of the chloro compound. The yield was 93%. Recrystallization gave the product having mp. 134° ~ 135° C (decomp).

EXAMPLE 9

Into a suspension of 38 g of potassium 6-phenylacetamidopenicillanate and 1 g of potassium hydrogen carbonate were dropped 30 ml of dimethylformamide solution containing 22 g of N,N-dimethyl-α-bromoacetoacetamido with stirring. Stirring was continued at 40° C. After confirming the completion of reaction by TLC, the reaction mixture was subjected to oxidation with a theoretical amount of 40% of peracetic acid. After the reaction was completed, 100 ml of methylene chloride and 200 ml of ice-water were added to the reaction mixture, which then was adjusted to pH 7.2 with sodium hydrogen carbonate. The aqueous layer was treated several times with methylene chloride. The combined organic layers were washed with water, dried and distilled in vacuo to remove the solvent.

1'-(N,N-dimethylaminocarbonyl)-2'-oxopropan -1'-yl ester of 6-phenylacetamidopenicillanic acid 1-oxide was obtained as syrupy. Yield: 42.5 g (92%). It was treated with isopropyl alcohol and isopropyl ether to yield the crystals of mp 52° ~ 55° C and IR: 1800 cm$^{-}$.

EXAMPLE 10

Into a suspension of 38 g of potassium 6-phenylacetamidopenicillanate and 2 g of potassium hydrogen carbonate in 50 ml of dimethylsulfoxide and 40 ml of dimethylformamide, 18 g of α-chloro-N,N-dimethylacetoacetamide were added under stirring. The reaction was conducted at 40° ~ 60° C. When needed, a catalytic amount of sodium iodide was added. After 5 ~ 7 hours, 150 ml of methylene chloride and 200 ml of ice-water were added. The aqueous layer was saturated with sodium chloride and treated several times with methylene chloride. The combined organic layers were washed with water, dried and distilled in vacuo to remove the solvent. To a solution of the residue in methanol was added a catalytic amount of vanadium pentaoxide, which was oxidized with 30% hydrogen peroxide. If needed, further hydrogen peroxide will be added. After completing the oxidation, 50 ml of ice-water were added and the mixture was adjusted to pH 7.3. The methanol was removed in vacuo. The aqueous layer containing a precipitate was extracted with methylene chloride, and the extract was washed with water, dried and distilled in vacuo to remove the solvent. The residue was treated with isopropyl ether to solidify. Recrystallization from isopropyl alcohol and isopropyl ether gave crystals of mp 53° ~ 55° C, which was identical with that obtained in Example 9. Yield: 42 g (91%).

EXAMPLE 11

1'-(N,N-Dimethylaminocarbonyl)-2'-oxopropan-1'-yl ester of 6-phenoxyacetamidopenicillanic acid 1-oxide was prepared according to procedure described in Example 9, using potassium 6-phenoxyacetamidopenicillanate instead of potassium 6-phenylacetamidopenicillanate in Example 9.
mp 58° ~ 62° C (from ethanol and isopropyl ether)
Yield: 91% , IR: 1800 cm$^{-1}$.

EXAMPLE 12

To a suspension of 19 g of potassium 6-phenylacetamidopenicillanate and 0.5 g of sodium hydrogen carbonate in 30 ml of dimethylformamide were added 11 g of α-chloro-acetoacetylmorpholide under stirring. The reaction was conducted at 40° C. After monitoring the reaction mixture by TLC, 100 ml of methylene chloride were added and the mixture was treated peracetic acid. After the oxidation was completed, 100 ml of ice-water were added to the reaction solution and adjusted to pH 7.3. The aqueous layer was treated several times with methylene chloride. The organic layers were combined washed with water and dried. Evaporation of the solvent left 22 g of 1'-morpholinocarbonyl-2'-oxopropan-1'-yl ester of 6-phenylacetamidopenicillanic acid 1-oxide as syrupy. Recrystallization from isopropyl alcohol and isopropyl ether gave the crystals of mp 70° ~ 80° C.

EXAMPLE 13

1'-Morpholinocarbonyl-2'-oxopropan-1'-yl ester of 6-phenoxyacetamidopenicillanic acid 1-oxide was prepared according to the procedure described in Example 12, using potassium 6-phenoxyacetamidopenicillanate instead of potassium 6-phenylacetamidopenicillanate in Example 12. Yield: 92 % IR: 1800 cm$^{-1}$ mp 80 ~ 100° C

EXAMPLE 14

Into the mixture of 6-phenylacetamidopenicillanic acid 1-oxide (3.5 g), 1.11 g of N-methylmorpholine and 0.3 g of sodium hydrogen carbonate in 10 ml of dimethylformamide, 3-bromo-2,4-pentadione (1.97 g) was stirred in, drop by drop. The reaction was continued for 3 ~ 5 hours at ambient temperature, monitoring by TLC benzene:ethyl acetate, spraying on a solution of iodoazide and heating). 20 ml of methylene chloride were added, and the mixture was adjusted to pH 7.0. The aqueous layer was treated with methylene chloride. The organic layers were combined, washed with a small amount of an aqueous sodium chloride solution, dried over magnesium sulfate and distilled in vacuo to remove the solvent. The residue was treated with isopropanol and n-hexane and purified by silica-gel chromatography using benzene and ethyl acetate as an eluate. 2′,4′-Dioxopentan-3′-yl ester of 6-phenylacetamidopenicillanic acid 1-oxide having mp 134° ~ 135° C (recrystallized from ethanol and isopropyl ether) was obtained in a yield of 94%.
IR: 1795 cm$^{-1}$

EXAMPLES 17 ~ 21

Instead of 3-chloro-2,4-pentandione used in Example 15, various chloro compounds (Cl-CH (R$_2$)-COR$_1$) were used and treated in a similar way as Example 15. Esters of 6-phenylacetamidopenicillanic acid 1-oxide thus produced are as follows.

| Example No. | $-CH(R_2)-COR_1$, $R_2$ | Ester mp (°C) | 1-Oxide Yield (%) | IR(cm$^{-1}$) | UV λmax (n.m.) |
|---|---|---|---|---|---|
| 17 | —CH(COCH$_3$)COC$_6$H$_5$ | 61~65 | 94 | 1800 | 252 |
| 18 | —CH(COCH$_3$)COOC$_2$H$_5$ | syrupy | 96 | 1795 | 251 |
| 19 | —CH(COC$_6$H$_5$)COOC$_2$H$_5$ | 47~60 | 95 | 1800 | |
| 20 | —CH(COCH$_3$)CON(CH$_3$)$_2$ | 52~55 | 82 | 1800 | |
| 21 | —CH(COCH$_3$)CON⟨O⟩ | 70-80 | 81 | 1800 | |

55° ~ 60° C was thus obtained. Yield 93% IR (KBr): 1800 cm$^{-1}$. It was identical with the authentic sample.

EXAMPLE 15

Dried 6-phenylacetamidopenicillanic acid 1-oxide (3.50 g), 1.11 g of triethylamine and 0.3 g of potassium hydrogen carbonate were added to 50 ml of acetone and 10 ml of dimethylsulfoxide. To this solution were added 1.40 g of 3-chloro-2,4-pentandione and 5 mg of sodium iodide with stirring and under ice-cooling. After 30 mins. the temperature was raised to ambient temperature. The reaction was continued for about 12 hours, while monitoring by TLC. Then acetone was distilled off in vacuo and the residue was treated in accordance with Example 14.

2,4-Dioxopentan-3-yl ester of 6-phenylacetamidopenicillanic acid 1-oxide having mp 55° ~ 60° C was thus obtained in a yield of 4.26 g (95%). Its TLC and IR were the same as that of the authentic sample.

EXAMPLE 16

Instead of 3-chloro-2,4-pentandione in Example 15, α-chloroacetoacetic acid methyl ester was used and treated in a similar way as Example 15.

1′-Methoxycarbonyl-2-oxopropan-1-yl ester of 6-phenylacetamidopenicillanic acid 1-oxide having mp

EXAMPLES 22 ~ 28

Instead of 6-phenylacetamidopenicillanic acid 1-oxide and 3-chloro-2,4-pentandione used in Example 15, 6-phenoxyacetamidopenicillanic acid 1-oxide and various chloro compounds (Cl-CH(R$_3$)-COR$_1$) were used and treated in a similar way as Example 15.

Esters of 6-phenoxyacetamidopenicillanic acid 1-oxide thus produced are as follows.

| Example No. | $-CH(COR_1)-R_2$, R$_2$ | Ester mp(°C) | 1-oxide Yield (%) | IR(cm$^{-1}$) | UV λmax (n.m.) |
|---|---|---|---|---|---|
| 22 | —CH(COCH$_3$)$_2$ | 145~148** | 94 | 1795 | |
| 23 | —CH(COCH$_3$)COC$_6$H$_5$ | 65~85 | 93 | " | 252 |
| 24 | —CH(COCH$_3$)COOCH$_3$ | 64~66* | 94 | 1795 | |
| 25 | —CH(COCH$_3$)COOC$_2$H$_5$ | syrupy | 95 | " | |
| 26 | —CH(COC$_6$H$_5$)COOC$_2$H$_5$ | 54~62 | 94 | " | |
| 27 | —CH(COCH$_3$)CON(CH$_3$)$_2$ | 58~62 | 72 | " | |
| 28 | —CH(COCH$_3$)CON⟨O⟩ | 80~100 | 85 | " | |

*Anal.; C$_{21}$H$_{24}$N$_2$O$_8$S
**Anal. ;C$_{21}$H$_{24}$N$_2$O$_8$S
Calcd.; C 52.50, H 5.03, N 5.83; C 54.30, H 5.21, N 6.03
Found; C 52.62, H 5.07, N 5.81 ; C 54.52, H 5.26, N 6.00.

EXAMPLE 29

7.44 g (20 m mol) of potassium salt of 6-phenylacetamidopenicillanic acid (penicillin G) and 3.17 g (20.5 m mol) of 1-acetyl-phenacylchloride in 15 ml of dimethylformamide was stirred for about 10 hous at ambient temperature. After monitoring the reaction by TLC (benzene:ethyl acetate = 2:1, spraying on a solution of iodo azide as a coluting agent and heating), 30 ml of methylene chloride and 50 ml of ice-water were added to the reaction mixture, followed by adjustment to pH 7.2. After separating the organic layer, the aqueous layer was extracted three times with methylene chloride. The combined organic layer were washed with a sodium chloride solution and dried over magnesium sulfate. The solvent was removed in vacuo to give an oily residue, which then was dissolved in 20 of methylene chloride and oxidized with a calculated amount of 40% peracetic acid. The reaction was monitored by TLC, and if necessary, peracetic acid was supplemented 50 ml of ice-water were added to the mixture, followed by separaton of organic layer. The aqueous layer was extracted several times with methylene chloride. To the combined organic layers were added 20 ml of ice-water, followed by adjustment to pH 7.5 with a sodium carbonate solution. After separating off the aqueous layer, the organic layer was washed with a sodium chloride solution and dried over magnesium sulfate. The solvent was distilled off in vacuo and the resultant residue was treated with n-hexane to give a solid product.

1-Acetyl-phenyl ester of 6-phenylacetamidopenicillanic acid 1-oxide was thus obtained a yield of 8.80 g (94%). The product was recrystallized from i-propanol and n-hexane. mp 61 ~ 65° C.

IR (KBr): 1800 cm$^{-1}$ ($\beta$-lactam)
UV $\lambda$max: 252 n.m.

EXAMPLE 30

Instead of penicillin G potassium salt in Example 29, penicillin V potassium salt was used and treated in a similar way as Example 29.

1-Acetyl-phenacylester of 6-phenoxyacetamidopenicillanic acid 1-oxide was obtained in a yield of 91%. mp 65 ~ 85° C IR (KBr): 1795 cm$^{-1}$
UV $\lambda$max: 252 n.m.

EXAMPLE 31

Instead of 1-acetyl-phenacyl chloride in Example 29, 1-ethoxycarbonyl-phenacylchloride was used and treated in a similar way as Example 29, 1-Ethoxycarbonyl-phenacyl ester of 6-phenylacetamidopenicillanic acid 1-oxide was obtained in a yield of 94%.

mp 47° ~ 60° C
IR (KBr): 1800 cm$^{-1}$.

EXAMPLE 32

Instead of penicillin G potassium salt in Example 31, penicillin V potassium salt was used and treated in a similar way as Example 31.

1-Ethoxycarbonyl-phenacylester of 6-phenoxyacetamidopenicillanic acid 1-oxide was obtained in a yield of 91%.

mp 54° ~ 62° C.
IR (KBr): 1795 cm$^{-1}$ UV $\lambda$max: 250 n.m.

EXAMPLE 33

Instead of 1-acetyl-phenacyl chloride and dimethylformamide in EXAMPLE 29, dimethoxycarbonylmethylchloride and dimethylsulfoxide were used and treated in a similar way as Example 29.

Dimethoxycarbonylmethylester of 6-phenylacetamidopenicillanic acid 1-oxide was obtained in a yield of 94%.

mp 132° ~ 133° C IR (KBr): 1800 cm$^{-1}$ Anal.; C$_{21}$H$_{24}$O$_9$N$_2$S; Calcd.; C 52.50, H 5.03, N 5.83 Found: C 52.72, H 5.07, N 5.79.

EXAMPLE 34

Instead of dimethoxycarbonylmethylchloride in Example 33, chloroacetic acid methyl ester was used and treated in a similar way as Example 33.

Methoxycarbonylmethylester of 6-phenylacetamidopenicillanic acid 1-oxide was obtained in a yield of 93%.

mp 107° ~ 108.5° C IR (KBr): 1800 cm$^{-1}$ Anal.; C$_{19}$H$_{22}$O$_7$N$_2$S Calcd.; C 54.02, H 5.25, N 6.63 Found; C 53.96, H 5.18, N 6.59

EXAMPLE 35

Instead of chloroacetic acid methyl ester in Example 34, $\alpha$-chloropropionic acid methylester was used and treated in a similar way as Example 34.

1-Methoxycarbonyl-ethylester of 6-phenylacetamidopenicillanic acid 1-oxide was obtained in a yield of 89%.

mp 112° ~ 114° C IR (KBr): 1800 cm$^{-1}$ Calcd.; C 55.04, H 5.54, N 6.42 Found; C 54.75, H 5.54, N 6.29

EXAMPLE 36

Instead of 1-acety-phenacylchloride in EXAMPLE 29, monochloroacetone was used and treated in a similar way as Example 29.

Acetylmethylester of 6-phenylacetamidopenicillanic acid was obtained in a yield of 88%. mp 50° ~ 60° C IR (KBr): 1790 cm$^{-1}$

What I claim is:

1. A penicillin ester having the formula:

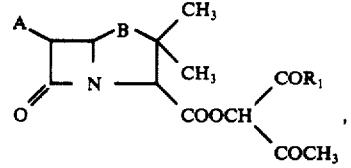

wherein A is a conventional penicillin acylamino group;
B is =S or =S—O; and
R$_1$ is methyl, methoxy or ethoxy.

2. A compound according to claim 1, in which A is phenylacetamido group.
3. A compound according to claim 1, in which A is phenoxyacetamido group.
4. 2',4'-Dioxopentan-3'-yl ester of 6-phenylacetamidopenicillanic acid or its 1-oxide according to claim 1.
5. 2',4'-Dioxopentan-3'-yl ester of 6-phenoxyacetamidopenicillanic acid or its 1-oxide according to claim 1.
6. 1'-methoxycarbonyl-2'-oxopropan-1'-yl ester of 6-phenylacetamidopenicillanic acid or its 1-oxide according to claim 1.
7. 1'-Methoxycarbonyl-2'-oxopropan-1'-yl ester of 6-phenoxyacetamidopenicillanic acid or its 1-oxide according to claim 1.
8. 1'-Ethoxycarbonyl-2'-oxopropan-1'-yl ester of 6-phenylacetamidopenicillanic acid or its 1-oxide according to claim 1.
9. 1'-Ethoxycarbonyl-2'-oxopropan-1'-yl ester of 6-phenoxyacetamidopenicillanic acid or its 1-oxide according to claim 1.

* * * * *